(12) United States Patent
Auclair (10) Patent No.: US 11,850,234 B2
(45) Date of Patent: Dec. 26, 2023

(54) ENHANCEMENT OF CANCER TREATMENT EFFICIENCY VIA THE SPHINGOSINE-1-PHOSPHATE PATHWAY

(71) Applicant: AC BIOSCIENCE, Ecublens (CH)

(72) Inventor: Christian Auclair, Saint-Arnoult-en-Yvelines (FR)

(73) Assignee: AC BIOSCIENCE, Ecublens (CH)

( * ) Notice: Subject to any disclaimer, the term of this patent is extended or adjusted under 35 U.S.C. 154(b) by 212 days.

(21) Appl. No.: 16/639,838

(22) PCT Filed: Aug. 17, 2018

(86) PCT No.: PCT/EP2018/072306
§ 371 (c)(1),
(2) Date: Feb. 18, 2020

(87) PCT Pub. No.: WO2019/034768
PCT Pub. Date: Feb. 21, 2019

(65) Prior Publication Data
US 2020/0261420 A1    Aug. 20, 2020

(30) Foreign Application Priority Data
Aug. 17, 2017 (EP) .................. 17306077

(51) Int. Cl.
*A61K 31/4164* (2006.01)
*A61P 35/00* (2006.01)
*A61K 45/06* (2006.01)

(52) U.S. Cl.
CPC .......... *A61K 31/4164* (2013.01); *A61P 35/00* (2018.01); *A61K 45/06* (2013.01)

(58) Field of Classification Search
None
See application file for complete search history.

(56) References Cited

FOREIGN PATENT DOCUMENTS

WO    99/16888 A2    4/1999
WO    03/097028 A1    11/2003

OTHER PUBLICATIONS

Kumar et al., Lyase to live by: Sphingosine phosphate lyase as a therapeutic target. Expert Opinion on Therapeutic Targets, 2009, 13, 1013-1025.*
Aguilar et al., Truth and consequence of sphingosine-1-phosphate lyase. Advances in Biological Regulation, 2012, 52, 17-30.*
Bagdanoff et al., "Inhibition of Sphingosine 1-Phosphate Lyase for the Treatment of Rheumatoid Arthritis: Discovery of (E)-1-(4-((1R,2S,3R)-1,2,3,4-Tetrahydroxybutyl)-1H-imidazol-2-yl)ethanone Oxime (LX2931) and (1R,2S,3R)-1-(2-(Isoxazol-3-yl)-1H-imidazol-4-yl)butane-1,2,3,4-tetraol (LX2932)", Journal of Medicinal Chemistry Article, Dec. 23, 2010, vol. 53, No. 24, pp. 8650-8662.

Laquente et al., "Antiangiogenic effect of gemcitabine following metronomic administration in a pancreas cancer model", Molecular Cancer Therapeutics, vol. 7, No. 3, Mar. 1, pp. 638-647.
International Search Report and Written Opinion of the International Searching Authority dated Oct. 31, 2018 in corresponding International application No. PCT/EP2018/072306; 15 pages.
Kunkel et al., "Targeting the sphingosine-1-phosphate axis in cancer, inflammation and beyond", Nature Reviews Drug Discovery, Sep. 2013, pp. 688-702; 30 pages.
Manggau et al., "Alpha,25-Dihydroxyvitamin D3 Protects Human Keratinocytes from Apoptosis by the Formation of Sphingosine-1-Phosphate", Journal of investigative dermatology, Nov. 2011, pp. 1241-1249; 9 pages.
Sultan et al., "Synergistic effect btween sphingosine-1-phosphate and chemotherapy drugs against human brain-metastasized breast cancer MDA-MB-361 cells", Journal of Cancer, Jan. 2013, pp. 315-319; 6 pages.
Blanke et al., "Phase II study of calcitriol-enhanced docetaxel in patients with previously untreated metastatic or locally advanced pancreatic cancer", Investigational new drugs ; The journal of new anticancer agents, Oct. 2009, pp. 374-378; 5 pages.
Gilzad Kohan et al., "Calcitriol reverses induced expression of efflux proteins and potentiates cytotoxic activity of gemcitabine in Capan-2 pancreatic cancer cells", Journal of pharmacy and pharmaceutical sciences, Aug. 2017, pp. 295-304; 10 pages.
Ma et al, "1,25D3 Enhances antitumor activity of gemcitabine and cisplatin in human bladder cancer models", Cancer, Apr. 2010, pp. 3294-3303; 10 pages.
Yu et al., "Calcitriol enhances gemcitabine antitumor activity in vitro and in vivo by promoting apoptosis in a human pancreatic carcinoma model system", Cell Cycle, Aug. 2010, pp. 3022-3029; 8 pages.
Ruckhäberle et al., "Predictive value of sphingosine kinase 1 expression in neoadjuvant treatment of breast cancer", Journal of cancer research and clinical oncology, Aug. 2013, pp. 1681-1689; 10 pages.
Grammatikos et al., "Serum sphingolipidomic analyses reveal an upregulation of C16-ceramide and sphingosine-1-phosphate in hepatocellular carcinoma", Oncotarget, Feb. 2016, pp. 18095-18105; 11 pages.
Brizuela et al., "First Evidence of Sphingosine 1-Phosphate Lyase Protein Expression and Activity Downregulation in Human Neoplasm: Implication for Resistance to Therapeutics in Prostate Cancer", Molecular Cancer Therapeutics, Jul. 2012, pp. 1841-1851; 12 pages.
Matula et al., "Regulation of cellular sphingosine-1-phosphate by sphingosine kinase 1 and sphingosine-1-phopshate lyase determines chemotherapy resistance in gastroesophageal cancer", BMC Cancer, Biomed Central, 2015, vol. 15; 14 pages.

* cited by examiner

*Primary Examiner* — Po-Chih Chen
(74) *Attorney, Agent, or Firm* — Maier & Maier, PLLC (57) ABSTRACT

The use of a neoadjuvant prior to chemotherapy. A sphingosine-1-phosphate pathway activator for use in the treatment of cancer as a neoadjuvant prior to chemotherapy selected from sphingosine-1-phosphate lyase inhibitors. The sphingosine-1-phosphate pathway activator enhances the chemotherapy efficiency through the normalization of intratumoral vascular network, promoting the effects of the sequential administration of an anticancer agent or a sequential radiotherapy.

8 Claims, 5 Drawing Sheets

|  | Median overall survival |
|---|---|
| S1P low (< 6.5 µM) | 6.9 months |
| S1P high (> 6.5 µM) | 12.3 months |

ENHANCEMENT OF CANCER TREATMENT EFFICIENCY VIA THE SPHINGOSINE-1-PHOSPHATE PATHWAY

FIELD

The present invention relates to the field of cancer treatment such as for example chemotherapy and radiotherapy as well as the enhancement of cancer treatment efficiency. More precisely, this invention relates to sphingosine-1-phosphate pathway activators for use in a method for enhancing efficacy of a chemotherapy or radiotherapy. The compounds for use in the method according to the invention, called neoadjuvants, are administrated to the subject prior to a subsequent chemotherapy or radiotherapy. According to the invention, the neoadjuvant is a sphingosine-1-phosphate lyase inhibitor.

BACKGROUND

Sphingosine-1-phosphate (S1P) is the product of phosphorylation of sphingosine by sphingosine kinase. Like many products of sphingomyelin, it exhibits a wide range of biological activities and can subsequently be involved in various diseases, conditions or disorders.

S1P has pleiotropic effects that on numerous pathologies including inflammation, diabetes, vascular diseases, (Bolick et al. Arterioscler Thromb Vasc Biol, 2005, 25, 976-981), multiple sclerosis, schizophrenia, haematological impairments, dermatological pathologies and cancers (Whetzel et al., Circulation research, 2006, 99, 731-739; Kunkel et al. Nat Rev Drug Discov, 2013, 12, 688-702).

Among the various possible actions, S1P can enhance cell growth and can inhibit the normal apoptotic response to a variety of stimuli. Manggau et al., J Clin Investig Dermatol, 2001, 117, pp 1241-1249) explain that calcitriol (1α,25-dihydroxyvitamin $D_3$) protects keratinocytes from apoptosis. One of the mechanisms of this calcitriol pharmacological effect is the activation of the sphingosine kinase activity, leading to increased levels of S1P.

There is a large set of evidence indicating that S1P is involved in cancer at multiple levels and involves S1P receptors, sphingosine kinase, S1P phosphatases and S1P lyase. Wang et al., (Mol cancer ther, 2008, 7, 1993-2002) shows that S1P stimulate migration and invasion of malignant epithelial ovarian cancer (EOC) cells but inhibit migration of non-malignant human ovarian surface epithelial (HOSE) cells. Secondly, Riccitelli et al., Plos one, 2013, 8(6):e68229, explains that extracellular S1P promotes the malignant properties of glioblastoma stem cells (GSC, being a cell subpopulation within the tumor) leading so to temolozomide resistance. Thirdly, Kunkel et al., Nat Rev Drug Discov, 2013, 12, 688-702 shows that S1P, aberrantly produced in ovarian cancer patients, is involved in the regulation of key cellular processes that contribute to ovarian cancer initiation and progression and, conversely, agents that block the S1P signaling pathway inhibit ovarian cancer cell growth. Kunkel et al., explains furthermore that S1P is known to the formation of functional blood vessels.

However, Sultan et al., Journal of cancer, 4, 2013, 315-319 discloses a synergistic effect of 10 μM of S1P co-administered with three different chemotherapy drugs with anti-angiogenic properties, namely docetaxel, doxorubicin and cyclophosphamide. This document discloses that S1P increased the cytotoxicity of these drugs against a breast cancer metastatic cell line.

Parallelly, WO 03/097028 discloses the biphasic effects of S1P receptor agonists in angiogenesis. On the one hand, high concentrations of S1P receptor agonists exhibit anti-angiogenic effects, useful in the treatment of cancer as they limit the vascularization of the tumors. On the other hand, the administration of low concentrations of S1P receptor agonists has an angiogenesis promoting effect. Angiogenesis promotion can be a useful in the treatment of non-cancer related diseases such as wound healing, myocardial irrigation pathologies or diabetes-related vascular dysfunctions. According to the WO 03/097028 disclosure, a S1P receptor agonist may be used alone or in combination with one or more further anticancer agents to produce a synergistic therapeutic effect. For example, S1P receptor agonist may be used in combination with a chemotherapeutic agent in the treatment of lymphatic or myeloid cancer.

Despite the evolution of pharmacology, the treatment of cancer is still an unmet need. More in particular, there is still a need to exploit the angiogenic properties of S1P in order to normalize the intratumoral vascular network and thereby improve the efficacy of any anticancer agent without anti-angiogenic properties. Therefore, the Applicant in search of new therapeutic approaches in the treatment of cancer, found a new method for the enhancing the efficacy of cancer treatment.

Contrary to the prior art evidence that S1P pathway inhibition leads to favorable regulation of key cellular processes that contribute to tumor initiation and progression to cancer, the Applicant observed that treated patients with elevated levels of plasmatic S1P concentrations, showed better overall survival rates. The activation of the S1P receptor 1 by S1P enhances the formation of adherent junctions, inhibits vascular endothelial growth factor signaling, suppresses sprouting and stabilizes new vascular connections.

The method according to the invention pertains to administrating a sphingosine-1-phosphate pathway activator as a neoadjuvant. The neoadjuvant according to the invention suppresses the sprouting angiogenesis and stabilizes the blood vessels. Consequently, the following chemotherapeutic agent has a better access to the tumor cells and therefore, an enhanced efficacy in its therapeutic effect. Likewise, the stabilization of the neovascular network improves the efficiency of a sequential anticancer radiotherapy.

SUMMARY

This invention relates to a method for improving the efficacy of a chemotherapy or radiotherapy treatment, comprising administering to a subject in need thereof a compound, called neoadjuvant, prior to the chemotherapy or radiotherapy.

More in particular the invention relates to a compound for use in a method of treatment of cancer in a subject. According to the invention, the said compound is sphingosine-1-phosphate lyase inhibitor that suppresses the sprouting angiogenesis and stabilizes the blood vessels. The compound for use according to the invention is a neoadjuvant for use in the efficacy enhancement of a sequential chemotherapy.

The sphingosine-1-phosphate lyase inhibitor is selected from a group consisting of 1-desoxy-dihydrosphingosine-1-phosphonate; 2-vinylsphinganine-1-phosphate; N-(4-(1H-imidazol-1-yl)benzyl)-4-amino-5-oxo-2-(piperidin-1-yl)-8-((tetrahydrofuran-2-yl)methyl)-5,8-dihydropyrido[2,3-d]pyrimidine-6-carboxamide; (R)-1-benzyl-4-(3-methyl-4-(p-tolyl)piperazin-1-yl)phthalazine; (R)-4-(4-(4-benzyl-7- chlorophthalazin-1-yl)-2-methylpiperazin-1-yl)benzonitrile; (R)-1-benzyl-4-(4-(4-cyanophenyl)-3-methyl-piperazin-1-yl)phthalazine-6-carbonitrile, 5-(hydroxymethyl)-2,4-dimethyl-pyridin-3-ol, and a compound of formula (I)

wherein
R1 represents H, acetyl, propanoyl, N-hydroxyacetimidoyl, isoxazol-3-yl, 4,5-dihydroisoxazol-3-yl or pro-1-en-2-yl; said isoxazol-3-yl or 4,5-dihydroisoxazol-3-yl being optionally substituted by at least one alkyl, acetyl, haloalkyl, hydroxyalkyl, alkyloxy, alkylamino or nitro group.
R2 represents 1,2,3,4-tetrahydroxybutyl, hydroxymethyl, H, ethyl carboxylate, N-methyl carboxamide, 1,2 dihydroxyethyl, 1-hydroxyethyl, 2-hydroxypropan-2-yl or phosphates thereof; and
R3 represents H, methyl, ethyl, methoxy or alkyloxyalkyl.

In one embodiment, the sphingosine-1-phosphate lyase inhibitor is a compound of formula (I), wherein:
R1 represents acetyl, N-hydroxyacetimidoyl, isoxazol-3-yl or 4,5-dihydroisoxazol-3-yl,
R2 represents 1,2,3,4-tetrahydroxybutyl, hydroxymethyl, H, 1,2-dihydroxyethyl, 1-hydroxyethyl or 2-hydroxypropan-2-yl; and
R3 represents H or alkyl, preferably R3 represents H or methyl, even more preferably R3 represents H.

In one embodiment, the sphingosine-1-phosphate lyase inhibitor is selected from a group consisting of 2-acetyl-4(5)-tetrahydroxybutyl-imidazole, 1-(4-(1,2,3,4-tetrahydroxybutyl)-1H-imidazol-2-yl)ethanone oxime, 1-(2-(isoxazol-3-yl)-1H-imidazol-4-yl)butane-1,2,3,4-tetraol, 1-(4-(1-hydroxymethyl)-1H-imidazol-2-yl)ethanone, 1-(4-(hydroxymethyl)-1H-imidazol-2-yl)ethanone oxime, and (2-(isoxazol-3-yl)-1H-imidazol-4-yl)methanol.

In one embodiment, the sphingosine-1-phosphate lyase inhibitor is 2-acetyl-4(5)-tetrahydroxybutyl-imidazole.

The sequential chemotherapy according to the invention involves a single anti-cancer agent or a combination of anticancer agents. Preferably, none of these agents displays anti-angiogenic properties. In one embodiment, the sequential chemotherapy involves agents selected from a group consisting of gemcitabine, paclitaxel, cisplatin and oxaliplatin.

In one embodiment, the subject displays a sphingosine-1-phosphate plasmatic concentration less than the median sphingosine-1-phosphate plasmatic concentration value of healthy volunteers. Since the sphingosine-1-phosphate plasmatic concentration measurement is analytical-method-dependent, the plasmatic concentration is measured with the same experimental protocol in the subject and in the healthy volunteers.

In one embodiment, the subject of displays a sphingosine-1-phosphate plasmatic concentration inferior to 700 nM, preferably inferior to 650 nM.

In one embodiment, the cancer is a solid tumor cancer, preferably a pancreatic cancer, even more preferably, a pancreatic adenocarcinoma.

In a second aspect, the invention relates to an in vitro non-invasive method for predicting or monitoring the clinical outcome of the chemotherapy or the radiotherapy treatment of a subject affected with a solid tumor cancer, preferably a pancreatic cancer. The in vitro non-invasive method according to the invention comprises the steps of:
a) Detecting and quantifying the sphingosine-1-phosphate concentration, in a previously obtained plasma sample from the subject; and
b) Comparing the results obtained in step a) with a reference value; said reference value of sphingosine-1-phosphate being at least 10% or at least 15% less than the median sphingosine-1-phosphate plasmatic concentration value of healthy volunteers; wherein said plasmatic concentration is measured with the same experimental protocol in the subject and in the healthy volunteers.

In one embodiment, the reference value is 650 nM of sphingosine-1-phosphate.

In a third aspect, the invention relates to a solid tumor cancer prognosis kit for carrying out the in vitro prognosis method of the present invention, consisting of a set of reagents suitable for the purification and/or the quantification of the sphingosine-1-phosphate.

DETAILED DESCRIPTION

In the present invention, the following terms have the following meanings:
"alkyl" refers to a hydrocarbyl radical of formula $C_nH_{2n+1}$ wherein n is a number greater than or equal to 1. Generally, alkyl groups of this invention comprise from 1 to 5 carbon atoms, preferably from 1 to 4 carbon atoms. Alkyl groups may be linear or branched and may be substituted as indicated herein. Suitable alkyl groups include methyl, ethyl, propyl (n-propyl, i-propyl, n-butyl), butyl (i-butyl, s-butyl and t-butyl).
"alkylamino" refers monoalkylamino and dialkylamino groups designating —NHR and —NRR' wherein R and R are alkyl groups. In one embodiment, R and R' are identical or different alkyl groups.
"alkyloxy" or "alkoxy" refers to any alkyl-O— group.
"alkyloxyalkyl" refers to any alkyl-O-alkyl group. In one embodiment, alkyloxymethyl refers to methyloxymethyle group (MOM).
"anti-angiogenic" refers to a naturally occurring substance, drug, or other compound that can destroy or interfere with the fine network of blood vessels needed by tumors to grow and metastasize.
"apoptosis" refers to programmed cell death.

"agonist" is a molecule interacting with and activating a membrane receptor.

"neoadjuvant" is a product administered prior to a main treatment, with the intent of boosting the efficacy or increasing the effectiveness of the chemotherapy.

"Sphingosine-1-phosphate" or S1P is a signaling sphingolipid, also known as lysosphingolipid. It is also referred to as a bioactive lipid mediator. Sphingolipids form a class of lipids characterized by a particular aliphatic aminoalcohol, which is sphingosine.

Figure 1:
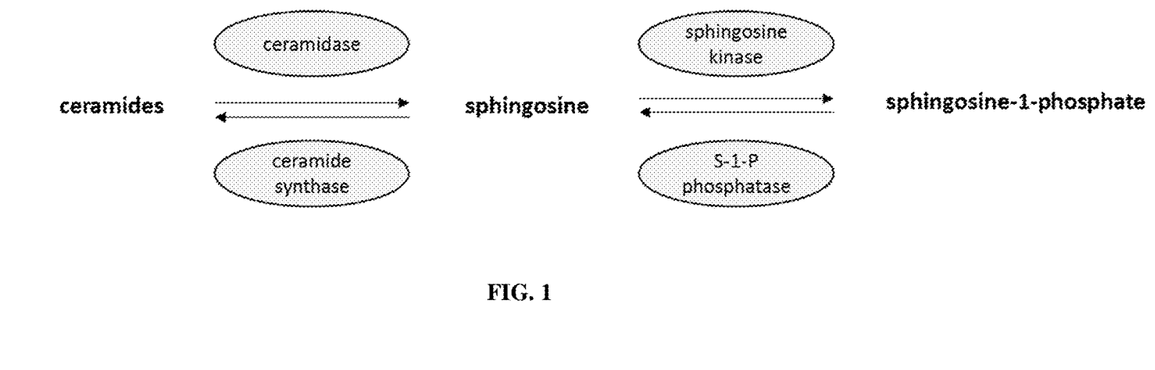
FIG. 1 is a schema showing the physiology of sphingosine-1-phosphate.

Phosphorylation of sphingosine to S1P is catalyzed by sphingosine kinase. S1P can be dephosphorylated to sphingosine by sphingosine phosphatases as depicted in FIG. 1. Furthermore, S1P can be degraded by an enzyme, sphingosine phosphate lyase.

"tumorigenic" qualifies a cell that can degenerate into a tumor.

"endothelial": endothelial cells are those that line the inner surface of the vessels. They are therefore cells which are in direct contact with the blood and which ensures the integrity of the vessels.

The invention relates to a compound for use in a method of treatment of cancer in a subject wherein the said compound is a sphingosine-1-phosphate pathway activator, wherein the compound for use suppresses the sprouting angiogenesis and stabilizes the blood vessels and wherein the compound for use according to the invention is a neoadjuvant for use in the efficacy enhancement of a sequential chemotherapy or radiotherapy. In one embodiment the compound for use is a sphingosine-1-phosphate pathway activator, enhancing the sphingosine-1-phosphate plasmatic concentration.

In one embodiment, the compound for use suppresses the sprouting angiogenesis and stabilizes the blood vessels and wherein the compound for use according to the invention is a neoadjuvant for use in the efficacy enhancement of a sequential chemotherapy.

Without willing to be bound by a theory, the effect of the neoadjuvants according to the present invention lead to the stabilization of the neovascular irrigation of the tumor. The enhanced oxygenation of the tumor cells enhances the efficacy of a subsequent radiotherapy to the subject in need thereof.

In one embodiment, the compound for use suppresses the sprouting angiogenesis and stabilizes the blood vessels and wherein the compound for use according to the invention is a neoadjuvant for use in the efficacy enhancement of a sequential radiotherapy.

The plasmatic concentration value of sphingosine-1-phosphate can be analytic-method and sex dependent.

In one embodiment, the subject displays a sphingosine-1-phosphate plasmatic concentration less than the median sphingosine-1-phosphate plasmatic concentration value of healthy volunteers; said plasmatic concentration being measured with the same experimental protocol in the subject and in the healthy volunteers.

In one embodiment, the subject displays a sphingosine-1-phosphate plasmatic concentration at least 10% or at least 15% less than the median sphingosine-1-phosphate plasmatic concentration value of healthy volunteers; said plasmatic concentration being measured with the same experimental protocol in the subject and in the healthy volunteers.

In one embodiment, the subject displays a sphingosine-1-phosphate plasmatic concentration inferior to 700 nM, preferably inferior to 650 nM, 600 nM, 550 nM, 500 nM, 450 nM, 400 nM, 350 nM, 300 nM, 250 nM, 200 nM, 150 nM, 100 nM, 50 nM or 10 nM. Preferably, the subject displays a sphingosine-1-phosphate plasmatic concentration inferior to 650 nM.

In one embodiment, the subject is a male subject and displays a sphingosine-1-phosphate plasmatic concentration inferior to 410 nM. In one embodiment, the subject is a female subject and displays a sphingosine-1-phosphate plasmatic concentration inferior to 350 nM.

In one embodiment, the subject is a male subject and displays a sphingosine-1-phosphate plasmatic concentration at least 5% or at least 10% inferior to 410 nM. In one embodiment, the subject is a female subject and displays a sphingosine-1-phosphate plasmatic concentration at least 5% or at least 10% inferior to inferior to 350 nM.

Compound for Use

The compound for use according to the invention is a sphingosine-1-phosphate pathway activator selected from a group comprising sphingosine-1-phosphate (S1P), sphingosine-1-phosphate lyase inhibitors, sphingosine-1-phosphate receptor agonists or sphingosine kinase activators.

In a first embodiment, the compound for use is sphingosine-1-phosphate.

According to a variant, the compound for use is sphingosine.

In a second embodiment, the compound for use is selected from a group comprising sphingosine-1-phosphate lyase inhibitors.

In one embodiment, the sphingosine-1-phosphate lyase inhibitors are selected from the group consisting of:

1-desoxy-dihydrosphingosine-1-phosphonate, 2-vinylsphinganine-1-phosphate,

N-(4-(1H-imidazol-1-yl)benzyl)-4-amino-5-oxo-2-(piperidin-1-yl)-8-((tetrahydrofuran-2-yl)methyl)-5,8-dihydropyrido[2,3-d]pyrimidine-6-carboxamide, (R)-1-benzyl-4-(3-methyl-4-(p-tolyepiperazin-1-yl) phthalazine, (R)-4-(4-(4-benzyl-7-chlorophthalazin-1-yl)-2-methylpiperazin-1-yl)benzonitrile, (R)-1-benzyl-4-(4-(4-cyanophenyl)-3-methylpiperazin-1-yl)phthalazine-6-carbonitrile, 5-(hydroxymethyl)-2,4-dimethylpyridin-3-ol (known as 4-deoxypyridoxine), and a compound of formula (I), wherein R1 represents H, acetyl, propanoyl, N-hydroxyacetimidoyl, isoxazol-3-yl, 4,5-dihydroisoxazol-3-yl or pro-1-en-2-yl; said isoxazol-3-yl or 4,5-dihydroisoxazol-3-yl being optionally substituted by at least one alkyl, acetyl, haloalkyl, hydroxyalkyl, alkyloxy, alkylamino or nitro group.

R2 represents 1,2,3,4-tetrahydroxybutyl, hydroxymethyl, H, ethyl carboxylate, N-methyl carboxamide, 1,2 dihydroxyethyl, 1-hydroxyethyl, 2-hydroxypropan-2-yl or phosphates thereof; and R3 represents H, methyl, ethyl, methoxy or alkyloxyalkyl.

In one embodiment, the sphingosine-1-phosphate lyase inhibitor is selected from the group consisting of:

N-(4-(1H-imidazol-1-yl)benzyl)-4-amino-5-oxo-2-(piperidin-1-yl)-8-((tetrahydrofuran-2-yl)methyl)-5,8-dihydropyrido[2,3-d]pyrimidine-6-carboxamide, (R)-1-benzyl-4-(3-methyl-4-(p-tolyepiperazin-1-yl) phthalazine, (R)-4-(4-(4-benzyl-7-chlorophthalazin-1-yl)-2-methylpiperazin-1-yl)benzonitrile (R)-1-benzyl-4-(4-(4-cyanophenyl)-3-methylpiperazin-1-yl)phthalazine-6-carbonitrile, and a compound of formula (I), wherein R1 represents acetyl, N-hydroxyacetimidoyl, isoxazol-3-yl, 4,5-dihydroisoxazol-3-yl or pro-1-en-2-yl;

R2 represents 1,2,3,4-tetrahydroxybutyl, hydroxymethyl, H, 1,2 dihydroxyethyl, 1-hydroxyethyl or 2-hydroxypropan-2-yl; and R3 represents H or alkyl, preferably R3 represents H or methyl, even more preferably R3 represents H.

In one embodiment, the sphingosine-1-phosphate lyase inhibitor is selected from the group consisting of:

(R)-1-benzyl-4-(3-methyl-4-(p-tolyl)piperazin-1-yl) phthalazine, (R)-4-(4-(4-benzyl-7-chlorophthalazin-1-yl)-2-methylpiperazin-1-yl)benzonitrile, (R)-1-benzyl-4-(4-(4-cyanophenyl)-3-methylpiperazin-1-yl)phthalazine-6-carbonitrile, and a compound of formula (I), wherein R1 represents acetyl, N-hydroxyacetimidoyl, isoxazol-3-yl or 4,5-dihydroisoxazol-3-yl;

R2 represents 1,2,3,4-tetrahydroxybutyl, hydroxymethyl, H, 1,2 dihydroxyethyl, 1-hydroxyethyl or 2-hydroxypropan-2-yl; and R3 represents H or alkyl, preferably R3 represents H or methyl, even more preferably R3 represents H.

In one embodiment, the sphingosine-1-phosphate lyase inhibitor is selected from the group consisting of:

(R)-1-benzyl-4-(3-methyl-4-(p-tolyl)piperazin-1-yl) phthalazine, (R)-4-(4-(4-benzyl-7-chlorophthalazin-1-yl)-2-methylpiperazin-1-yl)benzonitrile, (R)-1-benzyl-4-(4-(4-cyanophenyl)-3-methylpiperazin-1-yl)phthalazine-6-carbonitrile, and a compound of formula (I), wherein R1 represents acetyl, N-hydroxyacetimidoyl or isoxazol-3-yl;

R2 represents 1,2,3,4-tetrahydroxybutyl, hydroxymethyl, 1,2 dihydroxyethyl, 1-hydroxyethyl or 2-hydroxypropan-2-yl; and R3 represents H or alkyl, preferably R3 represents H or methyl, even more preferably R3 represents H.

In one embodiment, the sphingosine-1-phosphate lyase inhibitor is selected from the group consisting of:

(R)-1-benzyl-4-(3-methyl-4-(p-tolyl)piperazin-1-yl) phthalazine, (R)-4-(4-(4-benzyl-7-chlorophthalazin-1-yl)-2-methylpiperazin-1-yl)benzonitrile, (R)-1-benzyl-4-(4-(4-cyanophenyl)-3-methylpiperazin-1-yl)phthalazine-6-carbonitrile, and a compound of formula (I), wherein R1 represents acetyl or N-hydroxyacetimidoyl;

R2 represents 1,2,3,4-tetrahydroxybutyl, hydroxymethyl, 1,2-dihydroxyethyl, 1-hydroxyethyl or 2-hydroxypropan-2-yl; and R3 represents H or alkyl, preferably R3 represents H or methyl, even more preferably R3 represents H.

In one embodiment, the sphingosine-1-phosphate lyase inhibitor is selected from the group consisting of:

(R)-1-benzyl-4-(3-methyl-4-(p-tolyl)piperazin-1-yl) phthalazine, (R)-4-(4-(4-benzyl-7-chlorophthalazin-1-yl)-2-methylpiperazin-1-yl)benzonitrile, and (R)-1-benzyl-4-(4-(4-cyanophenyl)-3-methylpiperazin-1-yl)phthalazine-6-carbonitrile.

In one embodiment, the sphingosine-1-phosphate lyase inhibitor is (R)-1-benzyl-4-(3-methyl-4-(p-tolyl)piperazin-1-yl)phthalazine.

In one embodiment, the sphingosine-1-phosphate lyase inhibitor is (R)-4-(4-(4-benzyl-7-chlorophthalazin-1-yl)-2-methylpiperazin-1-yl)benzonitrile.

In one embodiment, the sphingosine-1-phosphate lyase inhibitor is (R)-1-benzyl-4-(4-(4-cyanophenyl)-3-methylpiperazin-1-yephthalazine-6-carbonitrile.

In one embodiment, the sphingosine-1-phosphate lyase inhibitor is selected from the group consisting of:

a compound of formula (I), wherein

R1 represents acetyl, N-hydroxyacetimidoyl, isoxazol-3-yl or 4,5-dihydroisoxazol-3-yl;

R2 represents 1,2,3,4-tetrahydroxybutyl, hydroxymethyl, H, 1,2-dihydroxyethyl, 1-hydroxyethyl or 2-hydroxypropan-2-yl; and R3 represents H or alkyl, preferably R3 represents H or methyl, even more preferably R3 represents H.

In one embodiment, the sphingosine-1-phosphate lyase inhibitor is selected from the group consisting of:

a compound of formula (I), wherein

R1 represents acetyl, N-hydroxyacetimidoyl or isoxazol-3-yl;

R2 represents 1,2,3,4-tetrahydroxybutyl, hydroxymethyl or H; and

R3 represents H or alkyl, preferably R3 represents H or methyl, even more preferably R3 represents H.

In one embodiment, the sphingosine-1-phosphate lyase inhibitor is selected from the group consisting of:

a compound of formula (I), wherein

R1 represents acetyl, N-hydroxyacetimidoyl or isoxazol-3-yl;

R2 represents 1,2,3,4-tetrahydroxybutyl or hydroxymethyl; and

R3 represents H or alkyl, preferably R3 represents H or methyl, even more preferably R3 represents H.

In one embodiment, the sphingosine-1-phosphate lyase inhibitor is selected from the group consisting of:

a compound of formula (I), wherein

R1 represents acetyl or N-hydroxyacetimidoyl;

R2 represents 1,2,3,4-tetrahydroxybutyl or hydroxymethyl; and

R3 represents H or alkyl, preferably R3 represents H or methyl, even more preferably R3 represents H.

In one embodiment, the sphingosine-1-phosphate lyase inhibitor is selected from the group consisting of:
a compound of formula (I), wherein
R1 represents acetyl or N-hydroxyacetimidoyl;
R2 represents hydroxymethyl; and
R3 represents H or alkyl, preferably R3 represents H or methyl, even more preferably R3 represents H.

In one embodiment, the sphingosine-1-phosphate lyase inhibitors are selected from the group of THI (2-acetyl-4 (5)-tetrahydroxybutyl-imidazole), metabolites and derivatives thereof. Thus, the sphingosine-1-phosphate lyase inhibitor may be selected from the group consisting of:
a compound of formula (I), wherein
R1 represents acetyl;
R2 represents 1,2,3,4-tetrahydroxybutyl, hydroxymethyl, H, 1,2 dihydroxyethyl, 1-hydroxyethyl or 2-hydroxypropan-2-yl; and
R3 represents H or alkyl, preferably R3 represents H or methyl, even more preferably R3 represents H.

In one embodiment, the sphingosine-1-phosphate lyase inhibitor is selected from the group consisting of:
a compound of formula (I), wherein
R1 represents acetyl;
R2 represents 1,2,3,4-tetrahydroxybutyl, hydroxymethyl or H; and
R3 represents H or alkyl, preferably R3 represents H or methyl, even more preferably R3 represents H.

In one embodiment, the sphingosine-1-phosphate lyase inhibitor is selected from the group consisting of:
a compound of formula (I), wherein
R1 represents acetyl;
R2 represents 1,2,3,4-tetrahydroxybutyl or hydroxymethyl; and
R3 represents H or alkyl, preferably R3 represents H or methyl, even more preferably R3 represents H.

In one embodiment, the sphingosine-1-phosphate lyase inhibitors are selected from the group of LX2931 (1-(4-(-1,2,3,4-tetrahydroxybutyl)-1H-imidazol-2-yl)ethanone oxime), metabolites and derivatives thereof. Thus, the sphingosine-1-phosphate lyase inhibitors may be selected from the group consisting of:
a compound of formula (I),

(I)

wherein
R1 represents N-hydroxyacetimidoyl;
R2 represents 1,2,3,4-tetrahydroxybutyl, hydroxymethyl, H, 1,2 dihydroxyethyl, 1-hydroxyethyl or 2-hydroxypropan-2-yl; and
R3 represents H or alkyl, preferably R3 represents H or methyl, even more preferably R3 represents H.

In one embodiment, the sphingosine-1-phosphate lyase inhibitor is selected from the group consisting of:
a compound of formula (I), wherein
R1 represents N-hydroxyacetimidoyl;
R2 represents 1,2,3,4-tetrahydroxybutyl, hydroxymethyl or H; and
R3 represents H or alkyl, preferably R3 represents H or methyl, even more preferably R3 represents H.

In one embodiment, the sphingosine-1-phosphate lyase inhibitor is selected from the group consisting of:
a compound of formula (I), wherein
R1 represents N-hydroxyacetimidoyl;
R2 represents 1,2,3,4-tetrahydroxybutyl or hydroxymethyl; and
R3 represents H or alkyl, preferably R3 represents H or methyl, even more preferably R3 represents H.

In one embodiment, the sphingosine-1-phosphate lyase inhibitors are selected from the group of LX2932 (1-(2-(isoxazol-3-yl)-1H-imidazol-4-yl)1,2,3,4-tetrahydroxybutyl), metabolites and derivatives thereof. Thus, the sphingosine-1-phosphate lyase inhibitors may be selected from the group consisting of:
a compound of formula (I), (I)

wherein
R1 represents isoxazol-3-yl;
R2 represents 1,2,3,4-tetrahydroxybutyl, hydroxymethyl, H, 1,2 dihydroxyethyl, 1-hydroxyethyl or 2-hydroxypropan-2-yl; and
R3 represents H or alkyl, preferably R3 represents H or methyl, even more preferably R3 represents H.

In one embodiment, the sphingosine-1-phosphate lyase inhibitors may be selected from the group consisting of:
a compound of formula (I), wherein
R1 represents isoxazol-3-yl;
R2 represents 1,2,3,4-tetrahydroxybutyl, hydroxymethyl or H; and
R3 represents or alkyl, preferably R3 represents H or methyl, even more preferably R3 represents H.

In one embodiment, the sphingosine-1-phosphate lyase inhibitors may be selected from the group consisting of:
a compound of formula (I), wherein
R1 represents isoxazol-3-yl;
R2 represents 1,2,3,4-tetrahydroxybutyl or hydroxymethyl; and
R3 represents or alkyl, preferably R3 represents H or methyl, even more preferably R3 represents H.

In one embodiment, the sphingosine-1-phosphate lyase inhibitors are selected from the group comprising:
1-desoxy-dihydrosphingosine-1-phosphonate,
2-vinylsphinganine-1-phosphate,
N-(4-(1H-imidazol-1-yl)benzyl)-4-amino-5-oxo-2-(piperidin-1-yl)-8-((tetrahydrofuran-2-yl)methyl)-5,8-dihydropyrido[2,3-d]pyrimidine-6-carboxamide,
(R)-1-benzyl-4-(3-methyl-4-(p-tolyl)piperazin-1-yl) phthalazine and derivatives thereof,
(R)-4-(4-(4-benzyl-7-chlorophthalazin-1-yl)-2-methylpiperazin-1-yl)benzonitrile,
(R)-1-benzyl-4-(4-(4-cyanophenyl)-3-methylpiperazin-1-yl)phthalazine-6-carbonitrile,
5-(hydroxymethyl)-2,4-dimethylpyridin-3-ol (known as 4-deoxypyridoxine),
2-acetyl-4(5)-tetrahydroxybutyl-imidazole (known as THI),
(E)-1-(4-(((1R,2S,3R)-1,2,3,4-tetrahydroxybutyl)-1H-imidazol-2-yl)ethanone oxime (known as LX2931), (1R,2S,3R)-1-(2-(isoxazol-3-yl)-1H-imidazol-4-yl)butane-1,2,3,4-tetraol (known as LX2932),
(1R,2S,3R)-1-(2-(4,5-dihydroisoxazol-3-yl)-1H-imidazol-4-yl)butane-1,2,3,4-tetraol,
1-(4-(hydroxymethyl)-1H-imidazol-2-yl)ethanone,
1-(1H-imidazol-2-yl)ethanone,
ethyl 2-acetyl-1H-imidazole-4-carboxylate,
2-acetyl-N-methyl-1H-imidazole-4-carboxamide,
1-(4-(1,2-dihydroxyethyl)-1H-imidazol-2-yl)ethanone,
1-(4-(1-hydroxyethyl)-1H-imidazol-2-yl)ethanone,
1-(4-(2-hydroxypropan-2-yl)-1H-imidazol-2-yl)ethanone,
1-(4-(hydroxymethyl)-1H-imidazol-2-yl)ethanone,
1-(4-(hydroxymethyl)-1-methyl-1H-imidazol-2-yl)ethanone,
1-(1-ethyl-4-(hydroxymethyl)-1H-imidazol-2-yl)ethanone,
1-(4-(hydroxymethyl)-1H-imidazol-2-yl)propan-1-one,
1-(4-(hydroxymethyl)-1H-imidazol-2-yl)ethanone oxime,
(2-(isoxazol-3-yl)-1H-imidazol-4-yl)methanol, and
(2-(prop-1-en-2-yl)-1H-imidazol-4-yl)methanol.

In one embodiment, the sphingosine-1-phosphate lyase inhibitors are selected from the group comprising:
(R)-1-benzyl-4-(3-methyl-4-(p-tolyl)piperazin-1-yl)phthalazine,
(R)-4-(4-benzyl-7-chlorophthalazin-1-yl)-2-methylpiperazin-1-yl)benzonitrile,
(R)-1-benzyl-4-(4-(4-cyanophenyl)-3-methylpiperazin-1-yl)phthalazine-6-carbonitrile,
5-(hydroxymethyl)-2,4-dimethylpyridin-3-ol (known as 4-deoxypyridoxine),
2-acetyl-4(5)-tetrahydroxybutyl-imidazole (known as THI),
(E)-1-(4-((1R,2S,3R)-1,2,3,4-tetrahydroxybutyl)-1H-imidazol-2-yl)ethanone oxime (known as LX2931),
(1R,2S,3R)-1-(2-(isoxazol-3-yl)-1H-imidazol-4-yl)butane-1,2,3,4-tetraol (known as LX2932),
1-(4-(hydroxymethyl)-1H-imidazol-2-yl)ethanone,
1-(4-(hydroxymethyl)-1H-imidazol-2-yl)propan-1-one,
1-(4-(hydroxymethyl)-1H-imidazol-2-yl)ethanone oxime, and
(2-(isoxazol-3-yl)-1H-imidazol-4-yl)methanol.

In one embodiment, the sphingosine-1-phosphate lyase inhibitors are selected from the group comprising:
1-desoxy-dihydrosphingosine-1-phosphonate,
-2-vinylsphinganine-1-phosphate,
N-(4-(1H-imidazol-1-yl)benzyl)-4-amino-5-oxo-2-(piperidin-1-yl)-8-((tetrahydrofuran-2-yl)methyl)-5,8-dihydropyrido[2,3-d]pyrimidine-6-carboxamide,
(R)-1-benzyl-4-(3-methyl-4-(p-tolyepiperazin-1-yl)phthalazine and derivatives thereof,
(R)-4-(4-(4-benzyl-7-chlorophthalazin-1-yl)-2-methylpiperazin-1-yl)benzonitrile,
(R)-1-benzyl-4-(4-(4-cyanophenyl)-3-methylpiperazin-1-yl)phthalazine-6-carbonitrile,
5-(hydroxymethyl)-2,4-dimethylpyridin-3-ol (known as 4-deoxypyridoxine),
2-acetyl-4(5)-tetrahydroxybutyl-imidazole (known as THI),
(E)-1-(4-((1R,2S,3R)-1,2,3,4-tetrahydroxybutyl)-1H-imidazol-2-yl)ethanone oxime (known as LX2931),
(1R,2S,3R)-1-(2-(isoxazol-3-yl)-1H-imidazol-4-yl)butane-1,2,3,4-tetraol (known as LX2932), and
(1R,2S,3R)-1-(2-(4,5-dihydroisoxazol-3-yl)-1H-imidazol-4-yl)butane-1,2,3,4-tetraol, In one embodiment, the sphingosine-1-phosphate lyase inhibitor is selected from the group comprising:
2-acetyl-4(5)-tetrahydroxybutyl-imidazole (known as THI),
(E)-1-(4-((1R,2S,3R)-1,2,3,4-tetrahydroxybutyl)-1H-imidazol-2-yl)ethanone oxime (known as LX2931), and
(1R,2S,3R)-1-(2-(isoxazol-3-yl)-1H-imidazol-4-yl)butane-1,2,3,4-tetraol,
Or a combination thereof.

In one embodiment, the sphingosine-1-phosphate lyase inhibitor is LX2931 (1-(4-(1,2,3,4-tetrahydroxybutyl)-1H-imidazol-2-yl)ethanone oxime). In one embodiment, the sphingosine-1-phosphate lyase inhibitor is LX2932 (1-(2-(isoxazol-3-yl)-1H-imidazol-4-yl)butane-1,2,3,4-tetraol). In one embodiment, the sphingosine-1-phosphate lyase inhibitor is the 2-acetyl-4(5)-tetra-hydroxybutyl-imidazole. In one embodiment, the sphingosine-1-phosphate lyase inhibitor is 1-(4-(1-hydroxymethyl)-1H-imidazol-2-yl)ethenone.

In one embodiment, the sphingosine-1-phosphate lyase inhibitor is selected from compound of formula (I) as previously described and active metabolites thereof.

In one embodiment, the sphingosine-1-phosphate lyase inhibitor is selected from a group consisting of:
2-acetyl-4(5)-tetrahydroxybutyl-imidazole,
1-(4-(1,2,3,4-tetrahydroxybutyl)-1H-imidazol-2-yl)ethanone oxime,
1-(2-(isoxazol-3-yl)-1H-imidazol-4-yl)butane-1,2,3,4-tetraol,
1-(4-(1-hydroxymethyl)-1H-imidazol-2-yl)ethanone,
1-(4-(1-hydroxyethyl)-1H-imidazol-2-yl)ethanone,
1-(4-(hydroxymethyl)-1H-imidazol-2-yl)ethanone oxime, and
(2-(isoxazol-3-yl)-1H-imidazol-4-yl)methanol.

In one embodiment, the sphingosine-1-phosphate lyase inhibitor is selected from a group consisting of:
2-acetyl-4(5)-tetrahydroxybutyl-imidazole,
1-(4-(1,2,3,4-tetrahydroxybutyl)-1H-imidazol-2-yl)ethanone oxime,
1-(2-(isoxazol-3-yl)-1H-imidazol-4-yl)butane-1,2,3,4-tetraol,
1-(4-(1-hydroxyethyl)-1H-imidazol-2-yl)ethanone,
1-(4-(hydroxymethyl)-1H-imidazol-2-yl)ethanone oxime, and
(2-(isoxazol-3-yl)-1H-imidazol-4-yl)methanol.

In one embodiment, the sphingosine-1-phosphate lyase inhibitor is selected from a group consisting of:
2-acetyl-4(5)-tetrahydroxybutyl-imidazole,
1-(4-(1,2,3,4-tetrahydroxybutyl)-1H-imidazol-2-yl)ethanone oxime,
1-(2-(isoxazol-3-yl)-1H-imidazol-4-yl)butane-1,2,3,4-tetraol,
1-(4-(1-hydroxymethyl)-1H-imidazol-2-yl)ethanone,
1-(4-(hydroxymethyl)-1H-imidazol-2-yl)ethanone oxime, and
(2-(isoxazol-3-yl)-1H-imidazol-4-yl)methanol.

In one embodiment, the sphingosine-1-phosphate lyase inhibitor is selected from a group consisting of:
2-acetyl-4(5)-tetrahydroxybutyl-imidazole,
1-(4-(1,2,3,4-tetrahydroxybutyl)-1H-imidazol-2-yl)ethanone oxime,
1-(4-(1-hydroxyethyl)-1H-imidazol-2-yl)ethanone, and
1-(4-(hydroxymethyl)-1H-imidazol-2-yl)ethanone oxime.

In one embodiment, the sphingosine-1-phosphate lyase inhibitor is selected from a group consisting of:
2-acetyl-4(5)-tetrahydroxybutyl-imidazole,
1-(4-(1,2,3,4-tetrahydroxybutyl)-1H-imidazol-2-yl)ethanone oxime, and
1-(4-(1-hydroxyethyl)-1H-imidazol-2-yl)ethanone.

The compounds were named using ChemBioDraw® Ultra version 12.0 (PerkinElmer).

N-(4-(1H-imidazol-1-yl)benzyl)-4-amino-5-oxo-2-(piperidin-1-yl)-8-((tetrahydrofuran-2-yl)methyl)-5,8-dihydropyrido[2,3-d]pyrimidine-6-carboxamide

(R)-1-benzyl-4-(3-methyl-4-(p-tolyl)piperazin-1-yl)phthalazine

(R)-4-(4-(4-benzyl-7-chlorophthalazin-1-yl)-2-methylpiperazin-1-yl)benzonitrile

(R)-1-benzyl-4-(4-(4-cyanophenyl)-3-methylpiperazin-1-yl)phthalazine-6-carbonitrile

5-(hydroxymethyl)-2,4-dimethylpyridin-3-ol

2-acetyl-4(5)-tetrahydroxybutyl-imidazole (known as THI)

(E)-1-(4-((1R,2S,3R)-1,2,3,4-tetrahydroxybutyl)-1H-imidazol-2-yl)ethanone oxime (known as LX2931)

(1R,2S,3R)-1-(2-(4,5-dihydroisoxazol-3-yl)-1H-imidazol-4-yl)butane-1,2,3,4-tetraol

(1R,2S,3R)-1-(2-(isoxazol-3-yl)-1H-imidazol-4-yl)butane-1,2,3,4-tetraol

1-(4-(hydroxymethyl)-1H-imidazol-2-yl)ethanone 1-(4-(1,2-dihydroxyethyl)-1H-imidazol-2-yl)ethanone 1-(4-(hydroxymethyl)-1H-imidazol-2-yl)ethanone oxime (2-(isoxazol-3-yl)-1H-imidazol-4-yl)methanol In a third embodiment, the compound for use is selected from a group comprising sphingosine kinase activators. In one embodiment, the sphingosine kinase activator is calcitriol (1α,25-dihydroxyvitamin $D_3$).

In a fourth embodiment, the compound for use is selected from a group comprising sphingosine-1-phosphate receptor agonists. In one embodiment the sphingosine-1-phosphate receptor agonist is selected from a group comprising:

- 2-amino-2-(4-octylphenethyl)propane-1,3-diol (known as Fingolimod or FTY720),
- 4-(4-(5-(5-chloro-6-isopropoxypyridin-3-yl)-1,2,4-oxadiazol-3-yl)-1H-indol-1-yl)butanoic acid (known as GSK 2018682),
- (2Z,5Z)-5-(3-chloro-4-((R)-2,3-dihydroxypropoxy)benzylidene)-2-(propylimino)-3-(o-tolyl)thiazolidin-4-one (known as Ponesimod),
- KRP-203,
- KRP-203,
- AUY954,
- ML178,
- XAX162,
- ML248,
- SEW2871,
- CYM5442,
- CYM5441,
- CYM5520,
- RP001,
- ASP4058,
- CS-0777,
- CS2100,
- BAF312,
- SID 46371153,
- AMG369, and
- phosphorylated derivatives thereof.

In one embodiment the sphingosine-1-phosphate receptor agonist is selected from a group comprising:

- 2-amino-2-(4-octylphenethyl)propane-1,3-diol (known as Fingolimod or FTY720),
- 4-(4-(5-(5-chloro-6-isopropoxypyridin-3-yl)-1,2,4-oxadiazol-3-yl)-1H-indol-1-yl)butanoic acid (known as GSK 2018682),
- (2Z,5Z)-5-(3-chloro-4-((R)-2,3-dihydroxypropoxy)benzylidene)-2-(propylimino)-3-(o-tolyl)thiazolidin-4-one (known as Ponesimod), and
- phosphorylated derivatives thereof.

In one embodiment the sphingosine-1-phosphate receptor agonist is selected from a group comprising FTY720 and phosphorylated FTY720 ((S)-(2-amino-2-(hydroxymethyl)-4-(4-octylphenyl)butyl)phosphonic acid or FTY720P). In one embodiment the sphingosine-1-phosphate receptor agonist is FTY720. In one embodiment the sphingosine-1-phosphate receptor agonist is FTY720P. In one embodiment the sphingosine-1-phosphate receptor agonist is GSK 2018682. In one embodiment the sphingosine-1-phosphate receptor agonist is Ponesidmod.

The compounds were named using ChemBioDraw® Ultra version 12.0 (PerkinElmer).

2-amino-2-(4-octylphenethyl)propane-1,3-diol (known as FTY720 or Fingolimod)

(S)-(2-amino-2-(hydroxymethyl)-4-(4-octylphenyl)butyl) phosphonic acid (known as FTY20P)

4-(4-(5-(5-chloro-6-isopropoxypyridin-3-yl)-1,2,4-oxadiazol-3-yl)-1H-indol-1-yl)butanoic acid (known as GSK 2018682)

(2Z,5Z)-5-(3-chloro-4-((R)-2,3-dihydroxypropoxy)benzylidene)-2-(propylimino)-3-(o-tolyl)thiazolidin-4-one (known as Ponesimod)

Method of Treatment

The invention relates to a compound for use in a method of treatment of cancer in a subject as a neoadjuvant.

The subject is a mammal, preferably a human. In one embodiment, a subject may be a is awaiting the receipt of, or is receiving medical care or was/is/will be the object of a medical procedure, or is monitored for the development of a disease.

In one embodiment, the subject is an adult (for example a subject above the age of 18). In another embodiment, the subject is a child (for example a subject below the age of 18). In one embodiment, the subject is a male. In another embodiment, the subject is a female.

In one embodiment, the subject is subjected to a primary therapy according the method of the invention. In one embodiment, the subject has not been responsive to a primary chemotherapy or radiotherapy treatment.

The compound for use as a neoadjuvant is administered prior to the administration of a sequential chemotherapy. In one embodiment, the compound for use as a neoadjuvant is administered at least once prior the sequential chemotherapy. In another embodiment, the neoadjuvant of the invention is administered in repeated doses prior the sequential chemotherapy.

In one embodiment, the at least one administration of the compound for use as a neoadjuvant of the invention takes place 16, 15, 14, 13, 12, 11, 10, 9, 8, 7, 6, 5, 4, 3,2 or 1 weeks prior the sequential chemotherapy. In one embodiment, the at least one administration of the neoadjuvant of the invention takes place 7, 6, 5, 4, 3,2 or 1 days prior the sequential chemotherapy. In one embodiment, the at least one administration of the neoadjuvant of the invention takes place 24, 23, 22, 21, 20, 19, 18, 17, 16, 15, 14, 13, 12, 11, 10, 9, 8, 7, 6, 5, 4, 3, 2 or 1 hours prior the sequential chemotherapy.

In one embodiment the neoadjuvant is administrated as a pharmaceutical composition comprising at least one of the compounds for use according to the invention together with one or more pharmaceutically acceptable diluents or carriers therefor.

The neoadjuvant may be administered by any conventional route, in particular enterally, e.g. orally, e.g. in the form of tablets, capsules, drink solutions, nasally, pulmonary or parenterally, e.g. in the form of injectable solutions or suspensions.

Suitable unit dosage forms for oral administration comprise from 0.01 to 1000 mg together with one or more pharmaceutically acceptable diluents or carriers. In order to suppress sprouting and stabilize new vascular connections in a tumor, a suitable dose for providing a vascular stabilizing effect when a neoadjuvant is administered to a subject may be selected by concentration- and dose-escalating studies as described in the art. In one embodiment, the dose of the neoadjuvant is adjusted in order to obtain a plasmatic concentration of sphingosine-1-phosphate superior to 650 nM.

The method of treatment of cancer, according to the invention, comprises the administration of a sequential chemotherapy to the subject, posterior to the administration of the neoadjuvant. In one embodiment, administration of a sequential chemotherapy comprises the administration of at least one anticancer agent. In one embodiment, the at least one anticancer agent is selected from a group consisting of paclitaxel, gemcitabine and oxaliplatin.

According to another embodiment the anticancer agent is a single agent or a combination of anticancer agents provided that none of these agents displays anti-angiogenic properties.

According to this embodiment, the anticancer agent is not a VEGF inhibitor, nor an EGFR inhibitor, nor a HER2 inhibitor, nor bevacizumad, nor cetuximab, nor panitumumab, nor trastuzumab. According to this embodiment the anticancer agent is not a VEGFR-1, nor a VEGFR-2 inhibitor, nor a VEGFR-3 inhibitor, nor a PDGF inhibitor, nor a c-kit inhibitor, nor a STAT3 inhibitor, nor a FGFR inhibitor, nor a RAF inhibitor, nor a TIMP 1 inhibitor, nor a TIMP 2 inhibitor, nor a TIMP 3 inhibitor, nor a metalloprotease inhibitor, nor cilengitide, nor erlotinib, nor sorafenib, nor sunitinib, nor gefitinib, nor lapatinib, nor pazopanib, nor mastinib, nor imatinib.

In a second aspect, the invention relates to a method of treatment of cancer using a sphingosine-1-phosphate (S1P) pathway activator as neoadjuvant prior to an anti-cancer therapy to improve the efficiency of the anticancer agent as described previously.

According to a first embodiment, the S1P pathway activator suppresses the sprouting angiogenesis and stabilizes the blood vessels of the tumor.

According to a second embodiment the sphingosine-1-phosphate pathway activator enhances the sphingosine-1-phosphate plasmatic concentration.

According to a third embodiment the sphingosine-1-phosphate pathway activator boosts the therapeutic effect of the anticancer agent.

In a third aspect, the invention relates to a method for improving efficacy of the treatment of a cancerous tumor in a subject in need thereof where:
  a. in a first step, the sphingosine-1-phosphate plasmatic concentration of the subject is measured,
  b. in a second step, administering an anti-cancer agent to a subject having a high S1P plasmatic level,
provided that the subject is not subjected to an anti-angiogenic agent.

In one embodiment, the treatment refers to a chemotherapy treatment. In one embodiment, the treatment refers to a radiotherapy treatment.

The plasmatic concentration value of sphingosine-1-phosphate can be analytic-method and sex dependent.

In one embodiment, the subject displays a sphingosine-1-phosphate plasmatic concentration less than the median sphingosine-1-phosphate plasmatic concentration value of healthy volunteers; said plasmatic concentration being measured with the same experimental protocol in the subject and in the healthy volunteers.

In one embodiment, the subject displays a sphingosine-1-phosphate plasmatic concentration at least 10% or at least 15% less than the median sphingosine-1-phosphate plasmatic concentration value of healthy volunteers; said plasmatic concentration being measured with the same experimental protocol in the subject and in the healthy volunteers.

In one embodiment, should the sphingosine-1-phosphate plasmatic concentration of the subject is inferior to 650 nM after the first step, the subject is receiving a neoadjuvant administration prior to the second step, as previously described.

The method of treatment according to any aspect of the invention can also be applied in combination with a further surgical intervention, mild prolonged whole body hyperthermia and/or irradiation therapy.

The method of treatment according to any aspect of the invention results in a beneficial effect such as slowing down, arresting or reversing the neoplasm formation, metastases spread or growth or a longer duration of tumor response. It may also result in other beneficial effects, such as the limitation of side-effects, an improved quality of life or a decreased mortality and morbidity, compared to a monotherapy applying only the chemotherapy agent.

The method of treatment according to any aspect of the invention concerns any type of cancer.

In a preferred embodiment the cancer is a solid tumorous cancer. In one embodiment the cancer is selected from a list comprising brain and other central nervous system tumors, head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors; respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e g malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites. Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is. In a preferred embodiment, the treatment according to any aspect of the invention concerns the treatment of pancreatic cancer, preferably pancreatic adenocarcinoma.

Solid Tumor Treatment Outcome Prognosis

In one aspect, the invention relates to sphingosine-1-phosphate for use in an in vitro non-invasive method for predicting the clinical outcome of the treatment of a subject; wherein the said method comprises:
a) Detecting and quantifying the sphingosine-1-phosphate concentration, in a previously obtained plasma sample from the subject, and
b) Comparing the results obtained in step a) with the median sphingosine-1-phosphate plasmatic concentration value of healthy volunteers; said plasmatic concentration being measured with the same experimental protocol in the subject and in the healthy volunteers.

In one embodiment, the method comprises:
a) Detecting and quantifying the sphingosine-1-phosphate concentration, in a previously obtained plasma sample from the subject, and
b) Comparing the results obtained in step a) with a reference value. The reference value being at least 10% or at least 15% less than the median sphingosine-1-phosphate plasmatic concentration value of healthy volunteers; said plasmatic concentration being measured with the same experimental protocol in the subject and in the healthy volunteers.

In one embodiment, the method comprises:
a) Detecting and quantifying the sphingosine-1-phosphate concentration, in a previously obtained plasma sample from the subject, and
b) Comparing the results obtained in step a) with the reference value 650 nM of sphingosine-1-phosphate.

In one embodiment, the method comprises:
a) Detecting and quantifying the sphingosine-1-phosphate concentration, in a previously obtained plasma sample from the subject, and
b) Comparing the results obtained in step a) with the reference value 410 nM of sphingosine-1-phosphate if the subject is male and 350 nM is the subject is female.

In one embodiment, the treatment refers to a chemotherapy treatment. In one embodiment, the treatment refers to a radiotherapy treatment.

In one embodiment, the subject suffers from a pancreatic cancer.

In another aspect, the invention relates to an in vitro non-invasive method for predicting the clinical outcome of the treatment of a subject; wherein the said method comprises:
a) Detecting and quantifying the sphingosine-1-phosphate concentration, in a previously obtained plasma sample from the subject, and
b) Comparing the results obtained in step a) with the reference value 650 nM of sphingosine-1-phosphate.

In one embodiment the treatment is a chemotherapy. In one embodiment the chemotherapy does not include agents with anti-angiogenic properties, as previously described.

In one embodiment, the subject is going to be subjected to a chemotherapy. In another embodiment, the subject is undergoing chemotherapy during the in vitro method of the present invention.

The Applicant has shown that subjects presenting a plasmatic concentration of sphingosine-1-phosphate superior to 650 nM, present a better clinical outcome after the administration of a chemotherapy.

Solid Tumor Prognosis Kit

In another aspect, the invention relates to a solid tumor cancer prognosis kit for carrying out the in vitro non-invasive method of the invention, consisting of a set of reagents suitable for the purification and/or the quantification of sphingosine-1-phosphate.

In one embodiment, the reagents are sphingosine-1-phosphate probes. In one embodiment, the reagents are selected from solvents, buffers, sphingosine-1-phosphate standard solutions, sphingosine-1-phosphate specific antibodies, labeled sphingosine-1-phosphate specific antibodies sphingosine-1-phosphate coated E.L.I.S.A (enzyme-linked immunosorbent assay) plaques. The purification and/or the quantification of sphingosine-1-phosphate can be carried out with techniques generally known in the art comprising but not limited to: centrifugation, solvent extraction, solid phase extraction, filtration, E.L.I.S.A. and other immune-enzymatic or immune-chemical techniques as well as chromatography techniques, preferably mass spectrometry coupled chromatography techniques.

EXAMPLES

The present invention is further illustrated by the following examples.

Example 1

Figure 2:
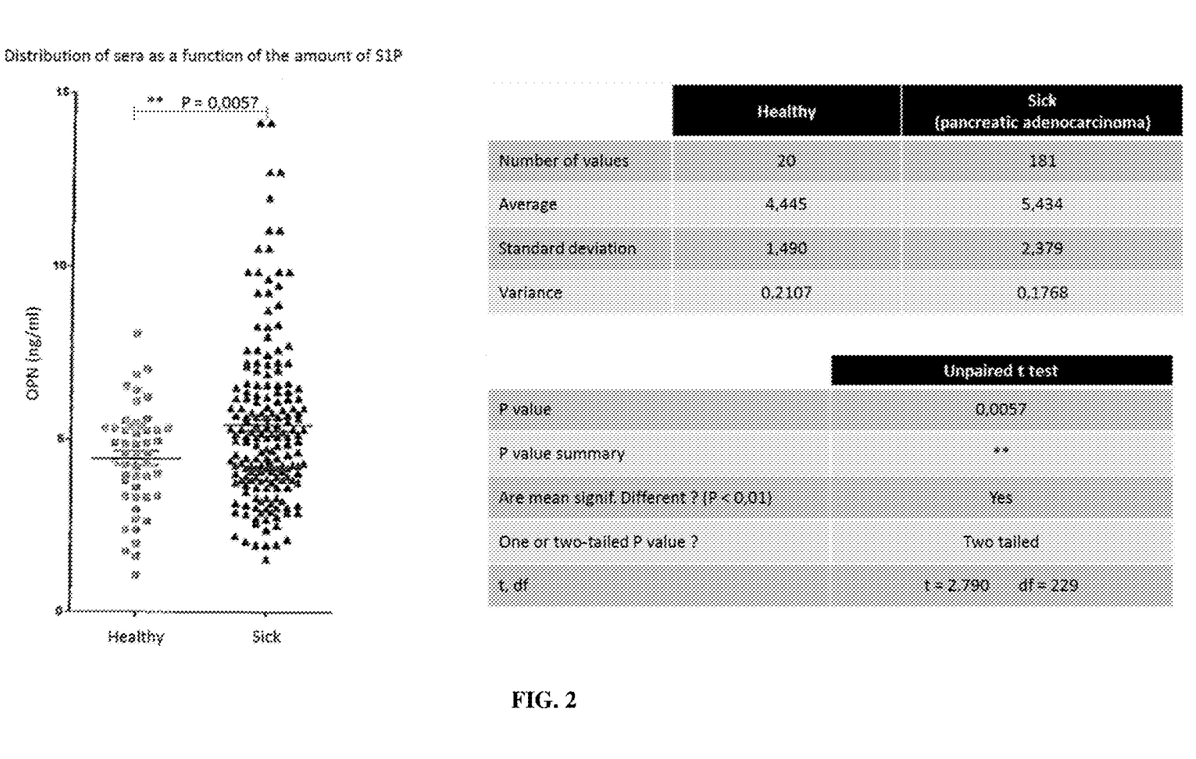
FIG. 2 comprises a graph and two tables showing S1P plasmatic concentrations at base line in patients diagnosed for a pancreatic adenocarcicoma compared to a healthy control group.

The S1P concentration was measured in the plasma sera of healthy individuals and pancreatic adenocarcinoma patients. It was observed that in patients suffering of a pancreatic adenocarcinoma, the S1P plasmatic concentration is significantly higher than the one measured in plasma of healthy volunteers as shown in FIG. 2.

Example 2

Figure 3:
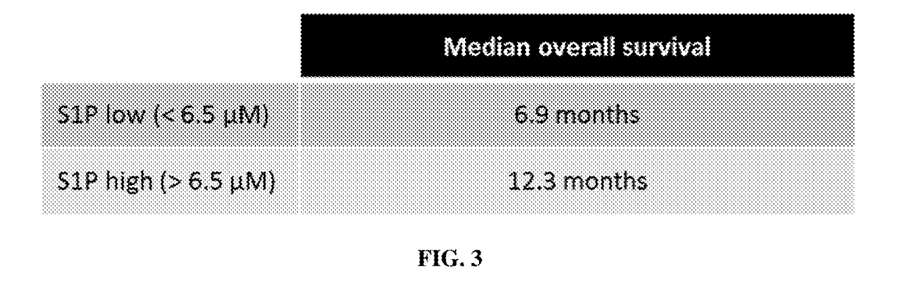
FIG. 3 is a table showing the median of overall survival in subgroups of patients displaying either "low" or "high" S1P plasmatic concentrations (p value: 0,05).

The plasmatic concentration of S1P is prognostic and predictive of treatment effect. Indeed, pancreatic adenocarcinoma suffering patients undergoing conventional gemcitabine chemotherapy showed a better overall survival median when their plasmatic concentration of S1P was higher than 650 nM. The results of this analysis are resumed in FIG. 3.

Figure 4:
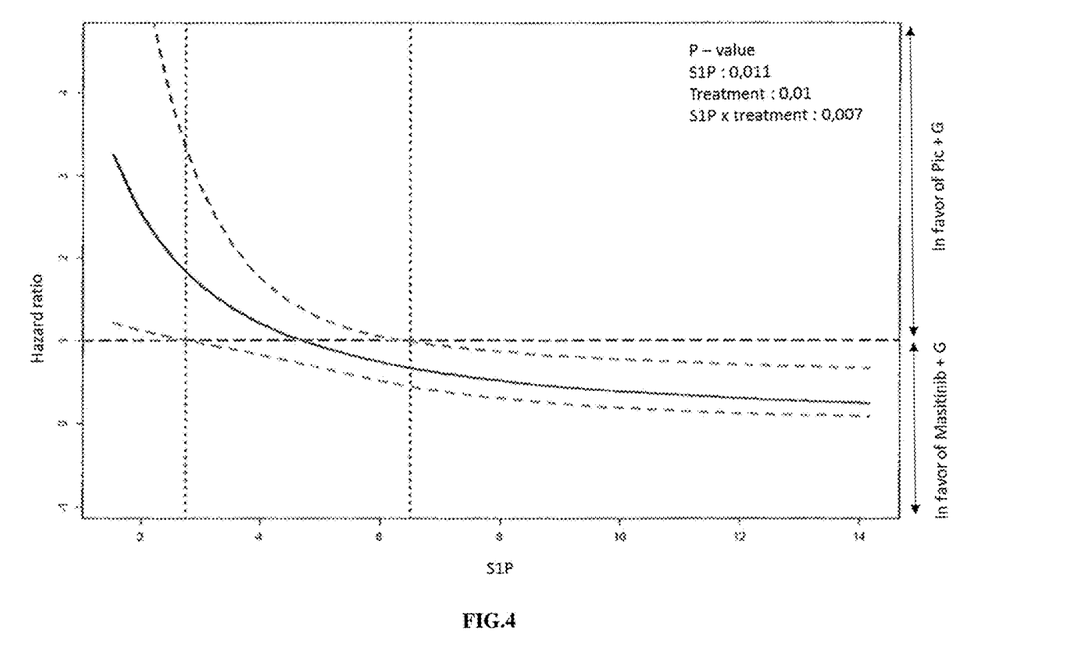
FIG. 4 is a graph showing the hazard ratio related to the overall survival as a function of plasmatic S1P concentration in patients treated by the conventional gemcitabine protocol.

When using S1P concentration as continuous variable, it can be observed that more S1P plasmatic concentration is high more the gemcitabine treatment is efficient (cf. FIG. 4).

A major point in relation with the present invention is that S1P, via the S1P receptor 1 suppresses the sprouting angiogenesis and stabilizes the blood vessels. According to this property, high S1P concentrations would normalize the tumor vessel network resulting in a better accessibility of the drug to the tumor. According to this property, all action resulting in an increase of plasmatic S1P concentration would normalize the tumor vessel network resulting in a better accessibility of the drug to the tumor.

Example 3

Figure 5:
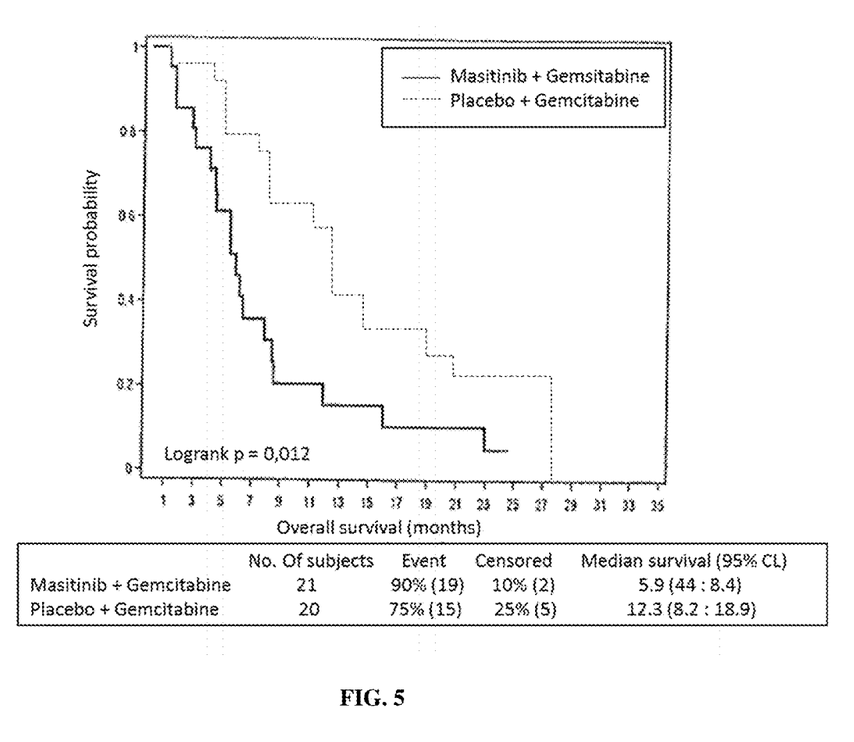
FIG. 5 is a graph showing the comparative overall survival median in patients having an S1P concentration higher than 650 nM and treated either by gemcitabine or by the combination gemcitabine+the kinase inhibitor masitinib.

In the subpopulation of patients having a high plasmatic S1P concentration (>650 nM), those treated by gemcitabine alone (arm gemcitabine+placebo) can be considered as good responder with an overall survival of 12.3 months. In contrast, those treated by the combination gemcitabine+kinase inhibitor (arm gemcitabine+masitinib) display a poor outcome with an overall of 5.9 months (cf. FIG. 5).

In fact, masitinib as imatinib are c-kit and PDGF (a and b) inhibitors and display anti-angiogenic properties leading to strong impairment of tumor vascular network. This effect antagonizes the action of S1P and in turn decreases the accessibility of gemcitabine to the tumor. The decrease of gemcitabine efficacy accompanied by the cumulative toxicity of both compounds result in a strong decrease of the overall survival of the patients enrolled in the arm gemcitabine+masitinib.

Example 4

The neoadjuvant effect of benzylphthalazine and imidazole derivatives according to the present invention are assessed for their neoadjuvant effect against pancreas, lung and ovarian tumors.

The neoadjuvant effect is evaluated using the CAM (Chicken Chorioallantoic Model) as described by Sliwinska et al. (Sliwinska et al., Angiogenesis, 2014, 14(4), 779-804).

Treatment with the compounds of the present invention leads to the stabilization of the neovascular network of the CAM-grafter tumors.

Furthermore, subsequent treating of the tumors with non-antiangiogenic chemotherapy shows an enhanced cytotoxic activity. More in particular, gemcitabine, paclitaxel and oxaliplatin cytotoxic effect against the pretreated CAM-grafted tumors was enhanced compared to the gemcitabine, paclitaxel and oxaliplatin treated CAM-grafted tumors which were not previously treated with the neoadjuvants according to the present invention.

The invention claimed is:

1. A method of treatment of pancreatic cancer presenting a sprouting angiogenesis of blood vessels in a subject in need thereof, comprising administering to said subject a therapeutically effective amount of 1-(4-(1,2,3,4-tetrahydroxybutyl)-1H-imidazol-2-yl)ethanone oxime to increase sphingosine-1-phosphate plasmatic concentration to a level in said subject to suppress the sprouting angiogenesis and stabilize the blood vessels; then administering a sequential chemotherapy involving gemcitabine;
wherein 1-(4-(1,2,3,4-tetrahydroxybutyl)-1H-imidazol-2-yl)ethanone oxime enhances efficacy of the sequential chemotherapy involving gemcitabine.

2. The method according to claim 1, wherein said sequential chemotherapy involves gemcitabine as a single anticancer agent or a combination of gemcitabine with one or more anticancer agents.

3. The method according to claim 1, wherein said sequential chemotherapy does not involve agents displaying anti-angiogenic properties.

4. The method according to claim 1, wherein the subject in need thereof displays a sphingosine-1-phosphate plasmatic concentration less than median sphingosine-1-phosphate plasmatic concentration value of healthy volunteers; said sphingosine-1-phosphate plasmatic concentration value of healthy volunteers being measured with an experimental protocol followed by a measurement of the sphingosine-1-phosphate plasmatic concentration in the subject with the same experimental protocol.

5. The method according to claim 1, wherein the subject in need thereof displays a sphingosine-1-phosphate plasmatic concentration of less than 700 nM prior to administering 1-(4-(1,2,3,4-tetrahydroxybutyl)-1H-imidazol-2-yl) ethanone oxime.

6. The method according to claim 1, wherein the subject in need thereof displays a sphingosine-1-phosphate plasmatic concentration of less than 650 nM prior to administering 1-(4-(1,2,3,4-tetrahydroxybutyl)-1H-imidazol-2-yl) ethanone oxime.

7. The method according to claim 1, wherein the pancreatic cancer is a pancreatic adenocarcinoma.

8. The method according to claim 1, wherein the efficacy enhancement is selected from a group of beneficial effects consisting of:
slowing down, arresting or reversing neoplasm formation, metastases spread or growth, or a longer duration of tumor response in the subject in need thereof,
limitation of side-effects, an improved quality of life or a decreased mortality and morbidity of the subject in need thereof,
when compared to a monotherapy applying only hemotherapy agent involving gemcitabine.

* * * * *